(12) United States Patent
Sambongi et al.

(10) Patent No.: US 9,948,865 B2
(45) Date of Patent: Apr. 17, 2018

(54) IMAGE PROCESSING APPARATUS, IMAGING DEVICE, AND IMAGE PROCESSING METHOD

(71) Applicants: OLYMPUS CORPORATION, Hachioji-shi, Tokyo (JP); NATIONAL UNIVERSITY CORPORATION CHIBA UNIVERSITY, Chiba-shi, Chiba (JP)

(72) Inventors: Masao Sambongi, San Jose, CA (US); Norimichi Tsumura, Chiba (JP); Kaori Baba, Tokyo (JP)

(73) Assignees: OLYMPUS CORPORATION, Tokyo (JP); NATIONAL UNIVERSITY CORPORATION CHIBA UNIVERSITY, Chiba-Shi, Chiba (JP)

( * ) Notice: Subject to any disclaimer, the term of this patent is extended or adjusted under 35 U.S.C. 154(b) by 0 days.

(21) Appl. No.: 15/467,699

(22) Filed: Mar. 23, 2017

(65) Prior Publication Data

US 2017/0195540 A1 Jul. 6, 2017

Related U.S. Application Data

(63) Continuation of application No. PCT/JP2015/074791, filed on Aug. 31, 2015.

(30) Foreign Application Priority Data

Sep. 29, 2014 (JP) ................................ 2014-198939

(51) Int. Cl.
*H04N 5/235* (2006.01)
*H04N 5/225* (2006.01)
(Continued)

(52) U.S. Cl.
CPC ............. *H04N 5/2352* (2013.01); *G02B 7/34* (2013.01); *G06K 9/4661* (2013.01);
(Continued)

(58) Field of Classification Search
CPC .... G02B 7/34; H04N 5/2256; H04N 5/23229; H04N 5/23296; H04N 5/2352;
(Continued)

(56) References Cited

U.S. PATENT DOCUMENTS

| | | | | |
|---|---|---|---|---|
| 8,412,359 B2* | 4/2013 | Boleko Ribas | ...... | H05B 37/029 700/11 |
| 2007/0009162 A1* | 1/2007 | Endo | ........................ | G02B 7/36 382/232 |

(Continued)

FOREIGN PATENT DOCUMENTS

| | | |
|---|---|---|
| JP | 11032251 A | 2/1999 |
| JP | 2006208333 A | 8/2006 |

(Continued)

OTHER PUBLICATIONS

International Search Report (ISR) and Written Opinion dated Nov. 24, 2015 issued in International Application No. PCT/JP2015/074791.

(Continued)

*Primary Examiner* — Amy Hsu
(74) *Attorney, Agent, or Firm* — Holtz, Holtz & Volek PC

(57) ABSTRACT

An image processing apparatus is intended to find, even when shooting a subject having a depth, respective reflection characteristics of portions of the subject with high accuracy, and includes a high-luminance region extraction unit which extracts high-luminance regions having a higher luminance than a predetermined threshold value in a plurality of image signals obtained by irradiating the subject with light emitted from a known light source and shooting reflected light from (Continued)

the subject at a plurality of viewpoints, a local region extraction unit which extracts local regions respectively most focused on in the portions of the subject using the plurality of high-luminance regions, and a reflection characteristic estimation unit which estimates a reflection characteristic of the subject using respective light source characteristics of the high-luminance regions in the local regions.

12 Claims, 13 Drawing Sheets

(51) Int. Cl.
    *H04N 5/232*     (2006.01)
    *H04N 5/355*     (2011.01)
    *H04N 5/3745*     (2011.01)
    *H04N 9/07*     (2006.01)
    *G06K 9/46*     (2006.01)
    *G02B 7/34*     (2006.01)

(52) U.S. Cl.
    CPC ......... *H04N 5/2256* (2013.01); *H04N 5/2356* (2013.01); *H04N 5/23229* (2013.01); *H04N 5/23296* (2013.01); *H04N 5/35572* (2013.01); *H04N 5/37455* (2013.01); *H04N 9/07* (2013.01)

(58) Field of Classification Search
    CPC ............. H04N 5/2356; H04N 5/35572; H04N 5/37455; H04N 9/07
    See application file for complete search history.

(56) References Cited

U.S. PATENT DOCUMENTS

| | | | | |
|---|---|---|---|---|
| 2008/0284885 A1* | 11/2008 | Taura | ...................... | H04N 5/335 348/300 |
| 2009/0304299 A1* | 12/2009 | Motomura | ............ | G06T 3/4007 382/254 |
| 2011/0019914 A1* | 1/2011 | Bimber | ................ | G02B 21/367 382/167 |
| 2011/0097067 A1* | 4/2011 | Osawa | .................... | G03B 7/097 396/165 |
| 2013/0058591 A1* | 3/2013 | Nishiyama | ............. | H04N 5/217 382/264 |
| 2013/0208175 A1* | 8/2013 | Ono | ........................ | G02B 3/14 348/344 |
| 2015/0002734 A1* | 1/2015 | Lee | ...................... | H04N 5/2256 348/367 |

FOREIGN PATENT DOCUMENTS

| | | |
|---|---|---|
| JP | 2006234613 A | 9/2006 |
| JP | 2008204318 A | 9/2008 |

OTHER PUBLICATIONS

Shinichi Inoue, et al., "Relationship between PSF and Gonio-reflectance Distribution of Specular Reflection", Proc. CGIV 2012, pp. 301-306.

\* cited by examiner

REFERENCE IMAGE SIGNAL

IMAGE SIGNAL 1

IMAGE SIGNAL 2

IMAGE OF LIGHT SOURCE S
REFLECTED ON SUBJECT P

ENLARGED IMAGE OF EDGE PORTION

ELECTRIC BULB

FLUORESCENT LIGHT

FLUORESCENT SOURCE

ELECTRIC BULB

FLUORESCENT LIGHT

FLUORESCENT SOURCE

FIG. 10
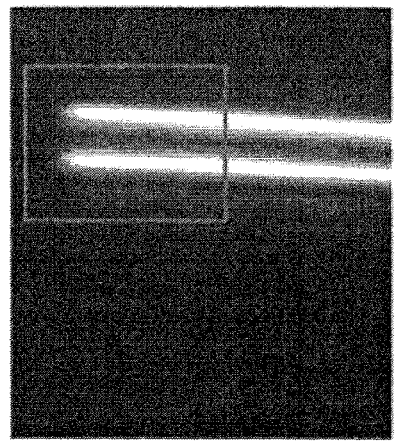
LIGHT SOURCE DISTRIBUTION
=
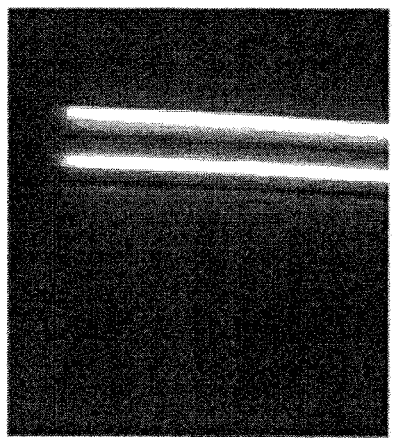
LIGHT SOURCE IMAGE
*
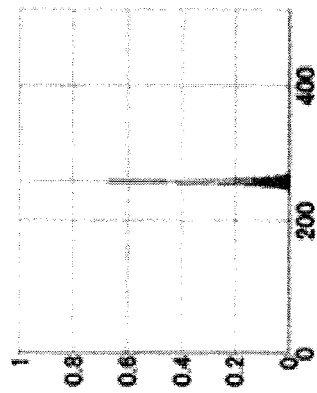
ESTIMATION OF
REFLECTION
CHARACTERISTIC

IMAGE PROCESSING APPARATUS, IMAGING DEVICE, AND IMAGE PROCESSING METHOD

CROSS-REFERENCE TO RELATED APPLICATIONS

This application is a Continuation application of International Application No. PCT/JP2015/074791 filed on Aug. 31, 2015, which claims priority to Japanese Application No. 2014-198939 filed on Sep. 29, 2014.
The contents of International Application No. PCT/JP2015/074791 and Japanese application No. 2014-198939 are hereby incorporated herein by reference in their entirety.

TECHNICAL FIELD

The present invention relates to an image processing apparatus, an imaging device, and an image processing method.

BACKGROUND ART

A method for estimating a reflection characteristic such as glossiness of an object from a one-shot image has been known (see, e.g., NPL 1). This method uses a point spread function of specular reflection indicating degree of defocus and estimates a reflection characteristic from a focused one-shot image.

CITATION LIST

Non Patent Literature

{NPL 1}
Inoue S., and Tsumura N., "Relationship between PSF and Gonioref reflectance distribution of Specular Reflection", Proc.CGIV, pp. 301-306, (2012)

SUMMARY OF INVENTION

According to an aspect of the present invention, there is provided an image processing apparatus, including a high-luminance region extraction unit which extracts high-luminance regions serving as regions each having a higher luminance than a predetermined threshold value in a plurality of image signals obtained by irradiating a subject with light emitted from a known light source and by shooting reflected light from the subject at a plurality of viewpoints different from one another, a local region extraction unit which extracts local regions each of which is in the most in-focus state in its portion of the subject using the plurality of high-luminance regions extracted in the high-luminance region extraction unit, and a reflection characteristic estimation unit which estimates a reflection characteristic of the subject using respective light source characteristics of the high-luminance regions in the local regions extracted in the local region extraction unit.

BRIEF DESCRIPTION OF DRAWINGS

FIG. 10 is a diagram illustrating an example of a light source distribution image generated by a light source distribution image generation unit in the imaging device illustrated in FIG. 8.

DESCRIPTION OF EMBODIMENTS

Figure 1:
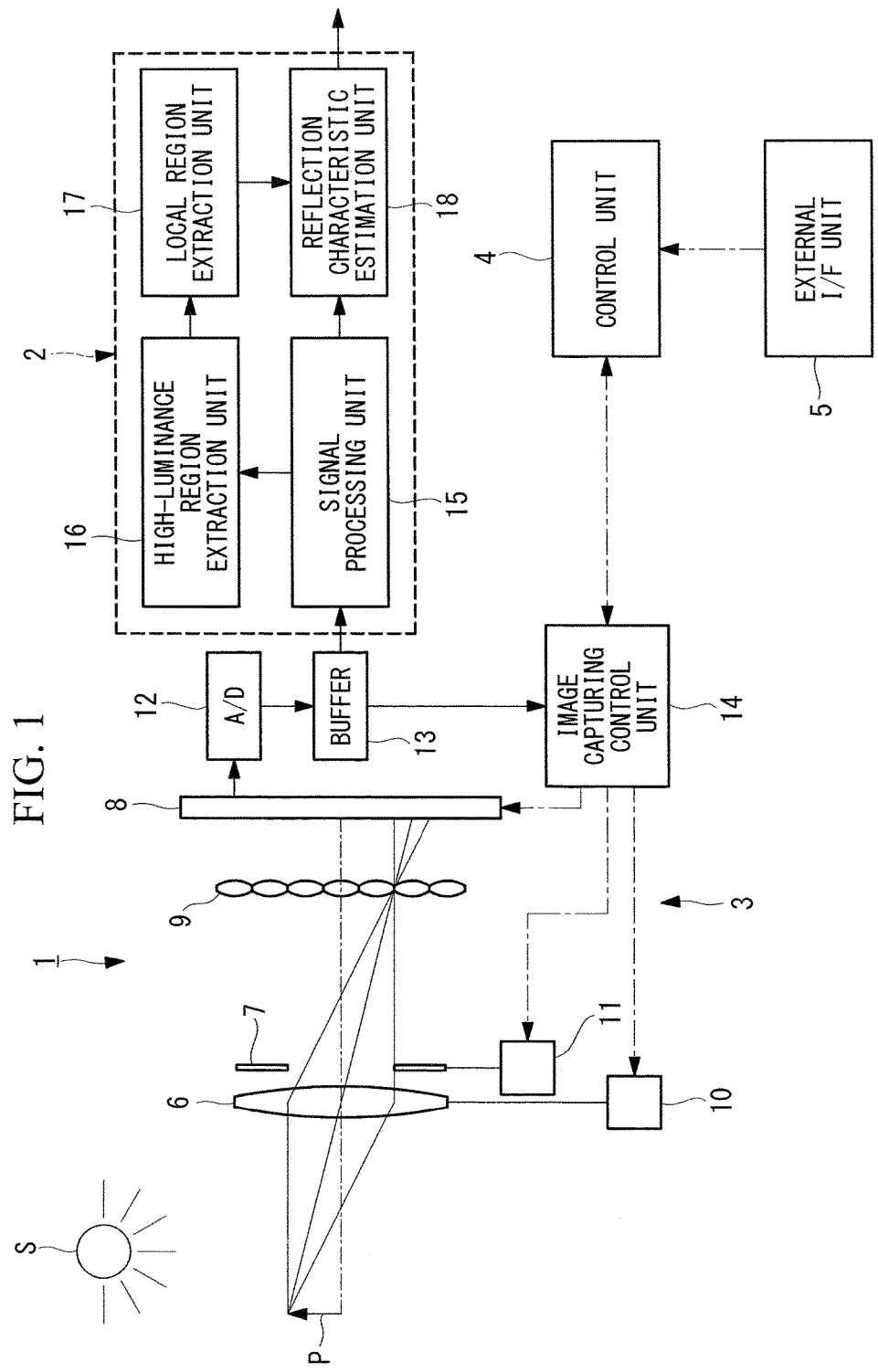
FIG. 1 is an overall view illustrating an imaging device according to a first embodiment of the present invention.

An imaging device 1, an image processing apparatus 2, and an image processing method according to a first embodiment of the present invention will be described below with reference to the drawings.
The imaging device 1 according to the present embodiment is a camera, and includes an image acquisition unit (image signal acquisition unit) 3, an image processing apparatus 2, a control unit 4 which controls the image acquisition unit 3 and the image processing apparatus 2, and an external I/F (interface) unit 5 which accepts an external input, as illustrated in FIG. 1.
The image acquisition unit 3 includes an imaging optical system (e.g., an imaging lens) 6 which collects light which is emitted from a light source S and then reflected by a subject P, a aperture 7, an image sensor 8 which captures the light collected by the imaging optical system 6, a microlens array 9 arranged between the image sensor 8 and the imaging optical system 6 and having a plurality of microlenses arranged therein in a two-dimensional manner in a direction intersecting an optical axis of the imaging optical system 6, an AF (automatic focus) motor 10 which moves the imaging optical system 6 in an optical axis direction, a aperture motor 11 which changes the opening size of the aperture 7, an A/D (analog-to-digital) conversion unit 12 which converts an image signal acquired by the image sensor 8 into a digital signal, a buffer 13 which stores the image signal, which has been converted into the digital signal, and an image capturing control unit 14.

When shooting conditions such as ISO (International Organization for Standardization) sensitivity and exposure are set via the external I/F unit 5, and a shutter button (not illustrated) is half-pressed, the imaging device 1 moves to a pre-shooting mode in which pre-shooting is performed by the image sensor 8. A pre-shot image signal acquired by the pre-shooting is stored in the buffer 13, and is transferred to the image capturing control unit 14 after being converted into a digital signal by the A/D conversion unit 12.

The image sensor 8 is a bayerCCD (Charge-Coupled Device) in an RGB (Red-Green-Blue) primary color system, for example. A CMOS (Complementary Metal Oxide Semiconductor) may be employed as the image sensor 8.

The image capturing control unit 14 calculates a focal length based on the pre-shot image signal, and drives the AF motor 10 and moves the imaging optical system 6 in the optical axis direction to focus on the subject P. The image capturing control unit 14 calculates the opening size of the aperture 7 for adjusting an amount of incident light and an electronic shutter speed of the image sensor 8 depending on a luminance level in the pre-shot image signal and a luminance level acquired by using a luminance sensor (not illustrated).

When the shutter button is fully pressed via the external I/F unit 5, main shooting is performed. In this case, the AF motor 10, the aperture motor 11, and the image sensor 8 are controlled based on the focal length acquired in the image capturing control unit 14 and an exposure condition while information during the image capturing is transferred to the control unit 4.

The microlens array 9 is arranged at a position where a real image of the subject P is formed. The real image formed in the microlens array 9 is further projected on the image sensor 8. Thus, the image sensor 8 can acquire an image having a plurality of parallax images arranged therein in an array shape. The image acquired by the image sensor 8 is sent to the image processing apparatus 2 after being converted into a digital signal by the A/D conversion unit 12.

The pre-processing apparatus 2 creates an image, which has been converted into the digital signal in the A/D conversion unit 12, at an appropriate position, to generate a plurality of parallax images included in the image while generating a plurality of image signals, which differ in focal position, by performing known re-focusing processing using the generated parallax images.

The image processing apparatus 2 includes a signal processing unit 15, a high-luminance region extraction unit 16, a local region extraction unit 17, and a reflection characteristic estimation unit 18.

The signal processing unit 15 creates the image, which has been converted into the digital signal in the A/D conversion unit 12, at an appropriate position, to generate a plurality of parallax images included in the image while generating a plurality of image signals, which differ in focal position, by performing known re-focusing processing using the generated parallax images. The signal processing unit 15 further reads the generated plurality of image signals in a single plate state and performs known demosaicing processing and white balance processing, to generate an RGB image signal in a three-plate state at each of pixels.

The high-luminance region extraction unit 16 first extracts a high-luminance region using, among the plurality of image signals processed by the signal processing unit 15, the one reference image signal. Then, the high-luminance region extraction unit 16 extracts, for the image signal different in focal position from the reference image signal, a region at the same position as that of the high-luminance region extracted for the reference image signal as a high-luminance region.

To extract the high-luminance region, a Y signal, which has been converted into a YCbCr signal, may be used, as indicated in an equation 1, or a G signal may be used as it Equation 1

$$\begin{bmatrix} Y \\ Cb \\ Cr \end{bmatrix} = \begin{bmatrix} 0.299 & 0.587 & 0.114 \\ -0.169 & -0.331 & 0.500 \\ 0.500 & -0.419 & -0.081 \end{bmatrix} \begin{bmatrix} R \\ G \\ B \end{bmatrix} \quad (1)$$

The extraction of the high-luminance region by the high-luminance region extraction unit 16 is performed by comparing a signal value of the image signal of each of the pixels with a threshold value. When the image signal is composed of n bits, for example, r×2n is used as a threshold value, and the pixel having the image signal the signal value of which is not less than the threshold value is extracted as the high-luminance region. Here, a coefficient r represents a real number satisfying 0<r<1. For example, n=8 and r=0.9, the pixel having the image signal is extracted as the high-luminance region when the image signal has a signal value of not less than 230.

Figure 2A:
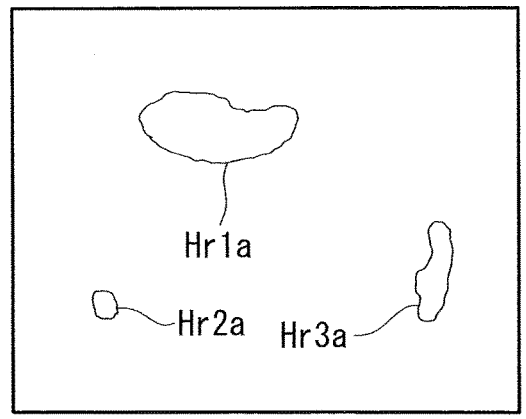
FIG. 2A is a diagram illustrating high-luminance regions in a reference image signal extracted by a high-luminance region extraction unit in the imaging device illustrated in FIG. 1.
Figure 2B:
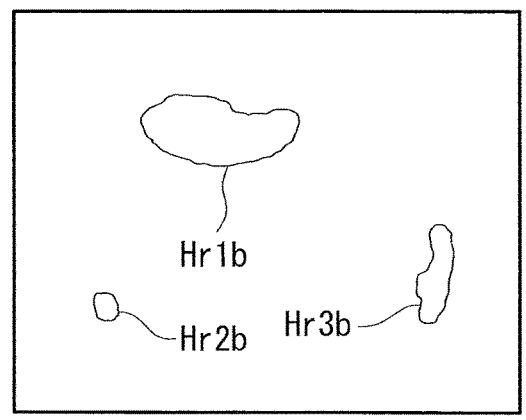
FIG. 2B is a diagram illustrating high-luminance regions in an image signal 1 which differs in focal position from that illustrated in FIG. 2A.
Figure 2C:
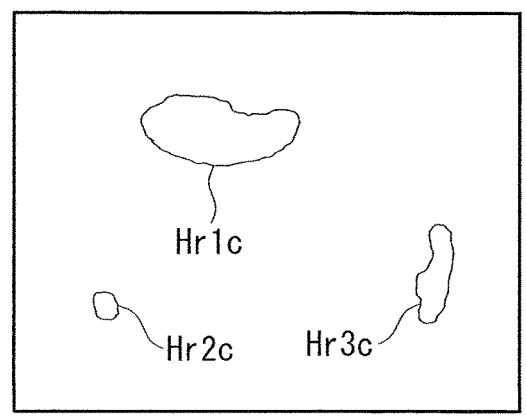
FIG. 2C is a diagram illustrating high-luminance regions in an image signal 2 which differs in focal position from those illustrated in FIGS. 2A and 2B.

FIG. 2A illustrates a high-luminance region extracted for the reference image signal. In an illustrated example, three high-luminance regions Hr1a, Hr2a, and Hr3a are extracted. FIGS. 2B and 2C respectively illustrate, for other two image signals which differ in focal position, high-luminance regions Hr1b, Hr2b, and Hr3b and high-luminance regions Hr1c, Hr2c, and Hr3c respectively extracted at the same positions as those of the corresponding high-luminance regions Hr1a, Hr2a, and Hr3a extracted for the reference image signal.

The local region extraction unit 17 respectively calculates, for all the high-luminance regions extracted in the high-luminance region extraction unit 16, contrast values according to an equation 2, and compares the contrast values among the corresponding high-luminance regions.

Equation 2

$$C_i(x, y) = \frac{g_i(x, y \in \omega)_{max} - g_i(x, y \in \omega)_{min}}{g_i(x, y \in \omega)_{max} + g_i(x, y \in \omega)_{min}} \quad (2)$$

Here, $g_i(x, y \in \omega)$ max and $g_i(x, y \in \omega)$ min respectively represent a maximum value and a minimum value of an image signal in a high-luminance region $\omega$ of the image signal i, and x and y respectively represent coordinate values of the image signal.

The local region extraction unit 17 compares the contrast values, extracts a region where the contrast value is the highest as a local region focused on, and transfers information on the local region to the reflection characteristic estimation unit 18.

The reflection characteristic estimation unit 18 estimates a reflection characteristic of each of portions of the subject P based on the information on the local region sent from the local region extraction unit 17.

Here, the reflection characteristic estimation unit 18 estimates a point spread function of specular reflection (hereinafter also referred to as a SR-PSF) as the reflection characteristic.

More specifically, the reflection characteristic estimation unit 18 calculates the SR-PSF based on a light source characteristic of a known light source S, an image signal in the local region sent from the local region extraction unit 17, and a point spread function (hereinafter merely referred to as a PSF) of an optical system.

Figure 3A:
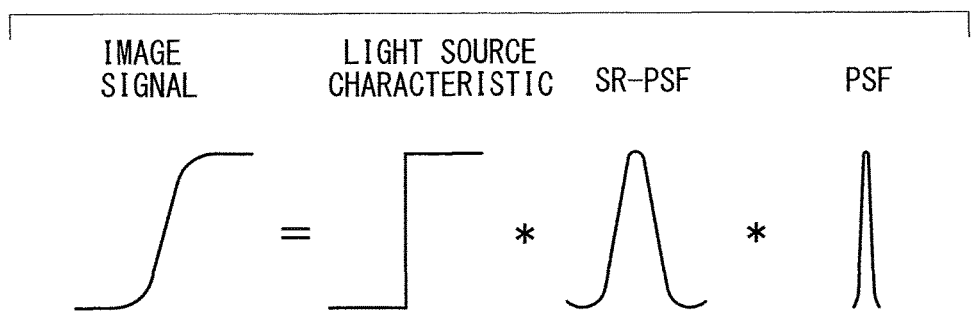
FIG. 3A is a diagram illustrating a model when a subject is focused on by a reflection characteristic estimation unit in the imaging device illustrated in FIG. 1.
Figure 3B:
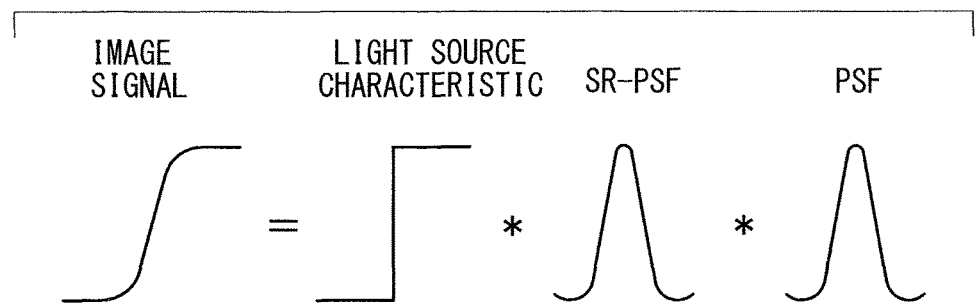
FIG. 3B is a diagram illustrating a model when a subject is not focused on by the reflection characteristic estimation unit in the imaging device illustrated in FIG. 1.

FIGS. 3A and 3B respectively illustrate models used to calculate the SR-PSF in the reflection characteristic estimation unit 18. For simplicity, a signal is one-dimensional.

Figure 4A:
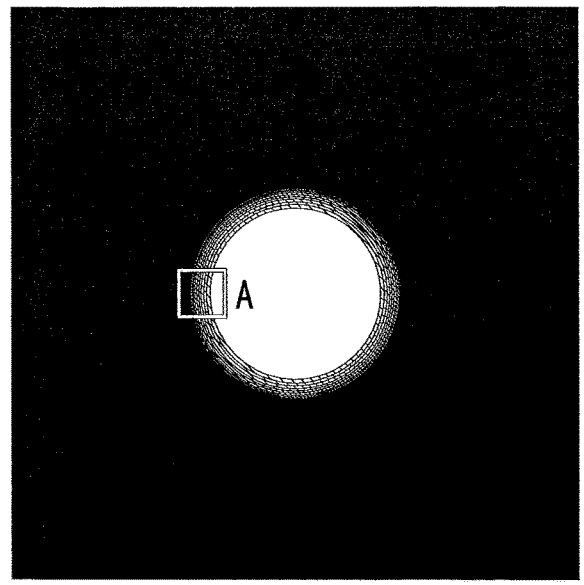
FIG. 4A is a diagram illustrating an image of a light source reflected on a subject captured by the imaging device illustrated in FIG. 1.
Figure 4B:
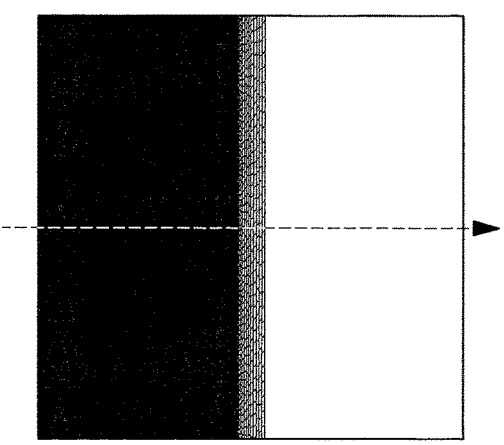
FIG. 4B is a diagram illustrating a part of an edge portion of the image illustrated in FIG. 4A in an enlarged manner.
Figure 5A:
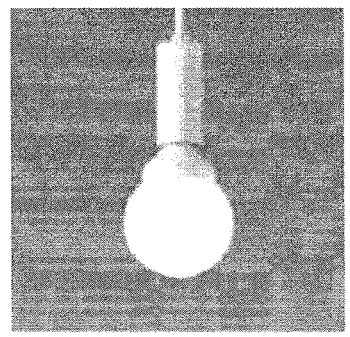
FIG. 5A is a diagram illustrating a picture of an electric bulb serving as a known light source.
Figure 5B:
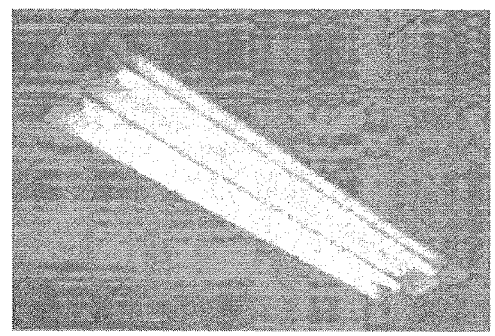
FIG. 5B is a diagram illustrating a picture of a fluorescent light serving as a known light source.
Figure 5C:
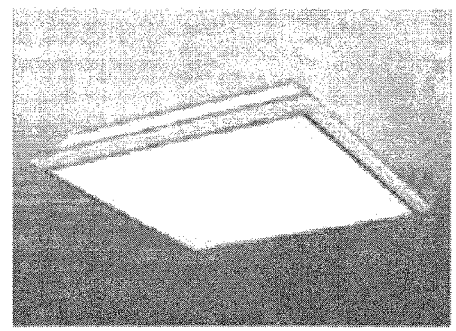
FIG. 5C is a diagram illustrating a picture of a fluorescent source serving as a known light source.
Figure 5D:
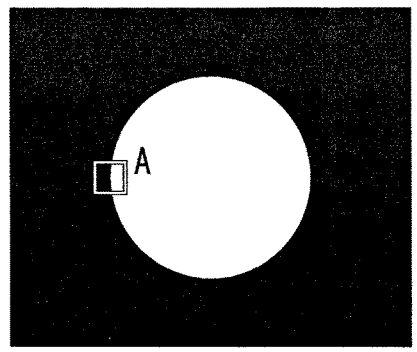
FIG. 5D is a diagram illustrating a light source characteristic of the electric bulb serving as a known light source.
Figure 5E:
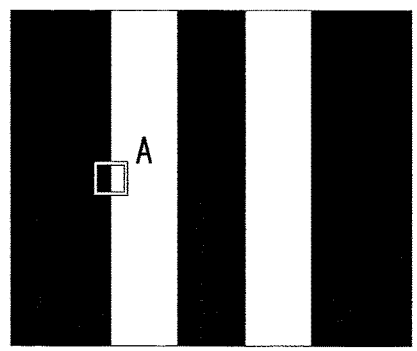
FIG. 5E is a diagram illustrating a light source characteristic of the fluorescent light serving as a known light source.
Figure 5F:
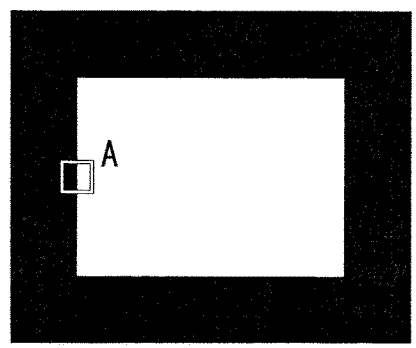
FIG. 5F is a diagram illustrating a light source characteristic of the fluorescent source serving as a known light source.
Figure 6:
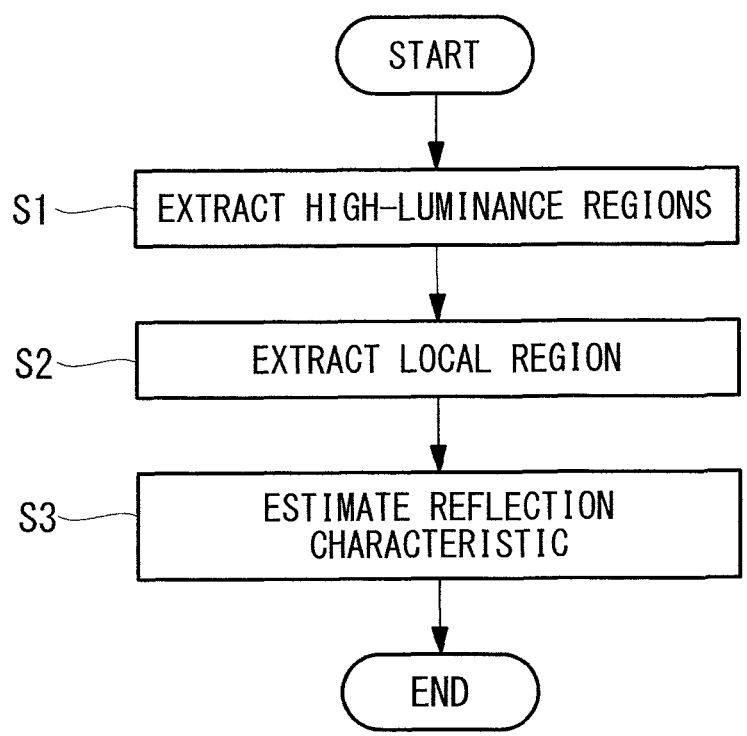
FIG. 6 is a diagram illustrating a flowchart of an image processing method according to the first embodiment of the present invention.

As illustrated in FIG. 1, when the light emitted from the known light source S is reflected on each of the portions of the subject P and is shot by the imaging device 1, the reflection characteristic of the subject P can be found by contrast between an image of the light source S reflected on the subject P as illustrated in FIGS. 4A and 4B and a light source characteristic of the known light source S as illustrated in FIGS. 5D to 5F. That is, in the model illustrated in each of FIGS. 3A and 3B, an image signal can be represented as a product of a light source characteristic, an SR-PSF, and a PSF. Therefore, the reflection characteristic estimation unit 18 estimates the SR-PSF from an equation 3 using this model.

Equation 3

$$g(x) = \int_{\infty}^{\infty} \int_{\infty}^{\infty} \{PSF_{SR}(x' - x)e(x')dx'\}PSF(x'' - x)dx'' \quad (3)$$
$$= \int_{0}^{\infty} PSF_{SR}(x' - x)e(x')dx'$$

Here, "PSFSR" represents an SR-PSF, and "PSF" represents a PSF of an optical system.

e (x) represents a light source characteristic including an edge as indicated in an equation 4.

Equation 4

$$e(x) = \begin{cases} 1 & x \geq 0 \\ 0 & x < 0 \end{cases} \quad (4)$$

When the equation 4 can be used as the light source characteristic, the equation 3 is changed into an equation 5.

$$g(x) = \int_0^x PSF_{SR}(x'')dx'' \quad \text{Equation 5}$$

Here, x"=x'−x Therefore, the equation 5 can be changed into an equation 6, and SR-PSF (x) serving as a function of x can be calculated by a primary differential of a signal value g (x).

Equation 6

$$PSF_{SR}(x) = \frac{dg(x)}{dx} \quad (6)$$

That is, in the model illustrated in each of FIGS. 3A and 3B, a characteristic of a region A in an edge portion of each of an image of the light source S reflected on the subject P illustrated in FIGS. 4A and 4B and a light source characteristic of a known light source S illustrated in FIGS. 5D to 5F is used. The known light source S, like an electric bulb illustrated in FIG. 5A, a fluorescent light illustrated in FIG. 5B, and a fluorescent source illustrated in FIG. 5C, has a light source characteristic in which its luminance changes in a stepped shape in the edge portion of the image of the light source S. On the other hand, the edge portion of the image of the light source S reflected on the subject P has a luminance distribution in which a stepped shape becomes dull in a dull manner corresponding to the reflection characteristic of the subject P. Thus, the reflection characteristic of the subject P can be extracted with high accuracy by using the characteristic of the region A in the edge portion.

An image processing method according to the present embodiment includes extracting high-luminance regions from a plurality of image signals, which differ in focal position, acquired in the image acquisition unit 3 (a high-luminance region extraction step S1), comparing the extracted high-luminance regions and extracting a local region having the highest contrast value (a local region extraction step S2), and estimating a reflection characteristic of the subject P by the models illustrated in FIGS. 3A and 3B using the extracted local region (a reflection characteristic estimation step S3).

That is, in the image processing method according to the present embodiment, the local region is extracted by comparing, among the plurality of image signals which differ in focal position, the high-luminance regions existing at the same regions to extract the local region. Thus, even if the respective depths of the portions of the subject P differ from one another, the local region focused on can be extracted in each of the portions.

The PSF is a defocus component of the optical system. When the subject P is not focused on, as illustrated in FIG. 3B, the PSF becomes an unknown function. Thus, the PSF is not easily estimated with high accuracy. However, when the subject P is focused on, the PSF can be considered as a delta function, as illustrated in FIG. 3A.

Thus, the image processing method according to the present embodiment has an advantage in that the local region focused on is extracted in each of the portions of the subject P, and thus the SR-PSF can be estimated simply and with high accuracy by the model illustrated in FIG. 3A using the delta function as the PSF.

In the imaging device 1 according to the present embodiment, the image acquisition unit 3 can acquire the plurality of image signals, which differ in parallax, by one shot, like in a known light field camera, using the microlens array 9. Therefore, the imaging device 1 according to the present embodiment is simply operated because the plurality of image signals, which differ in focal position, are generated using an acquired plurality of parallax images, and has an advantage in that the reflection characteristic of each of the portions of the subject P having a depth can be estimated simply and in a short time.

Figure 7:
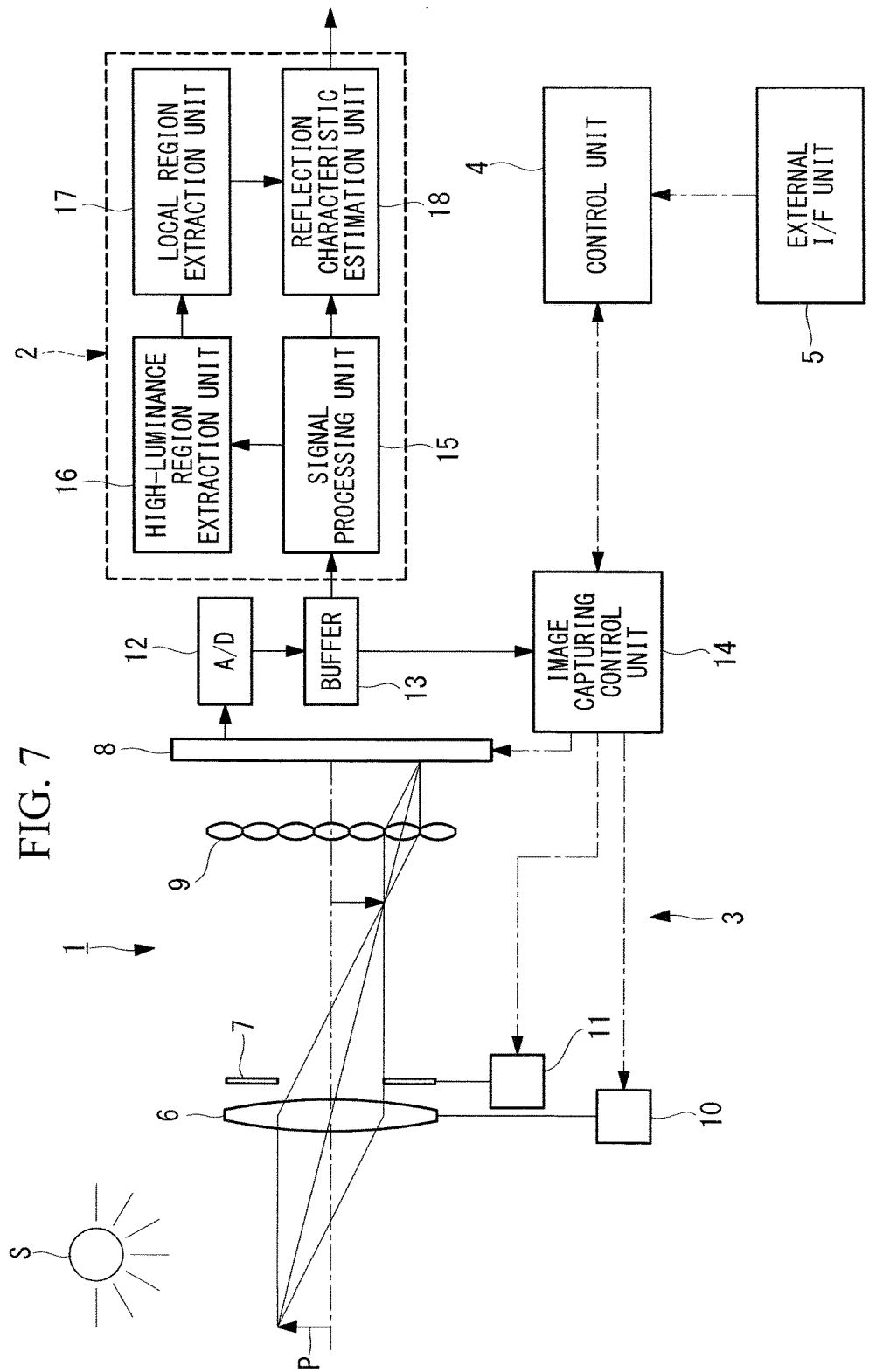
FIG. 7 is an overall view illustrating an imaging device according to a modification illustrated in FIG. 1.

In the present embodiment, description has been made of a case where the real image of the subject P is formed on the microlens array 9. However, this may be replaced with a configuration in which the microlens array 9 is arranged at a position spaced in the optical axis direction apart from the real image, as illustrated in FIG. 7.

In the present embodiment, an example in which the image acquisition unit 3 includes the microlens array 9 is illustrated. However, instead to this, a plurality of parallax images may be acquired by performing shooting a plurality of times while moving a single imaging optical system 6 having a large depth of field in a direction intersecting an optical axis direction.

A plurality of image signals, which differ in focal position, may be acquired by performing shooting a plurality of times while changing a focal position of a single imaging optical system 6 having a relatively small depth of field.

A plurality of parallax images may be acquired at one time by arranging a plurality of imaging optical systems 6 each having a large depth of field and an image sensor 8 in a direction intersecting an optical axis as the image acquisition unit 3.

While r2n is used as the threshold value in the high-luminance region extraction unit 16 in the present embodiment, r2n may be replaced with rM obtained by multiplying a maximum value M of a plurality of image signals by a coefficient r. A region of a small image signal may be excluded by performing known expansion and contraction processing for an image signal in an extracted high-luminance region.

While the local region focused on in each of the portions of the subject P is extracted from among the plurality of image signals in the local region extraction unit 17 in the present embodiment, the present invention is not limited to this. If a reference image signal having a large depth of field can be acquired by changing an F number of an optical system during shooting or the like, the SR-PSF may be estimated using only a high-luminance region in the reference image signal without performing processing by the local region extraction unit 17. Each of the parallax images acquired by shooting using the microlens array 9 also has a large depth of field. Thus, the SR-PSF may be similarly estimated using only a high-luminance region in any one of the parallax images.

An imaging device 19, an image processing apparatus 20, and an image processing method according to a second embodiment of the present invention will be described below with reference to the drawings.

In the description of the present embodiment, sites common in configuration to the imaging device 1, the image processing apparatus 2, and the image processing method according to the first embodiment, described above, are assigned the same reference numerals, and hence description thereof is not repeated.

Figure 8:
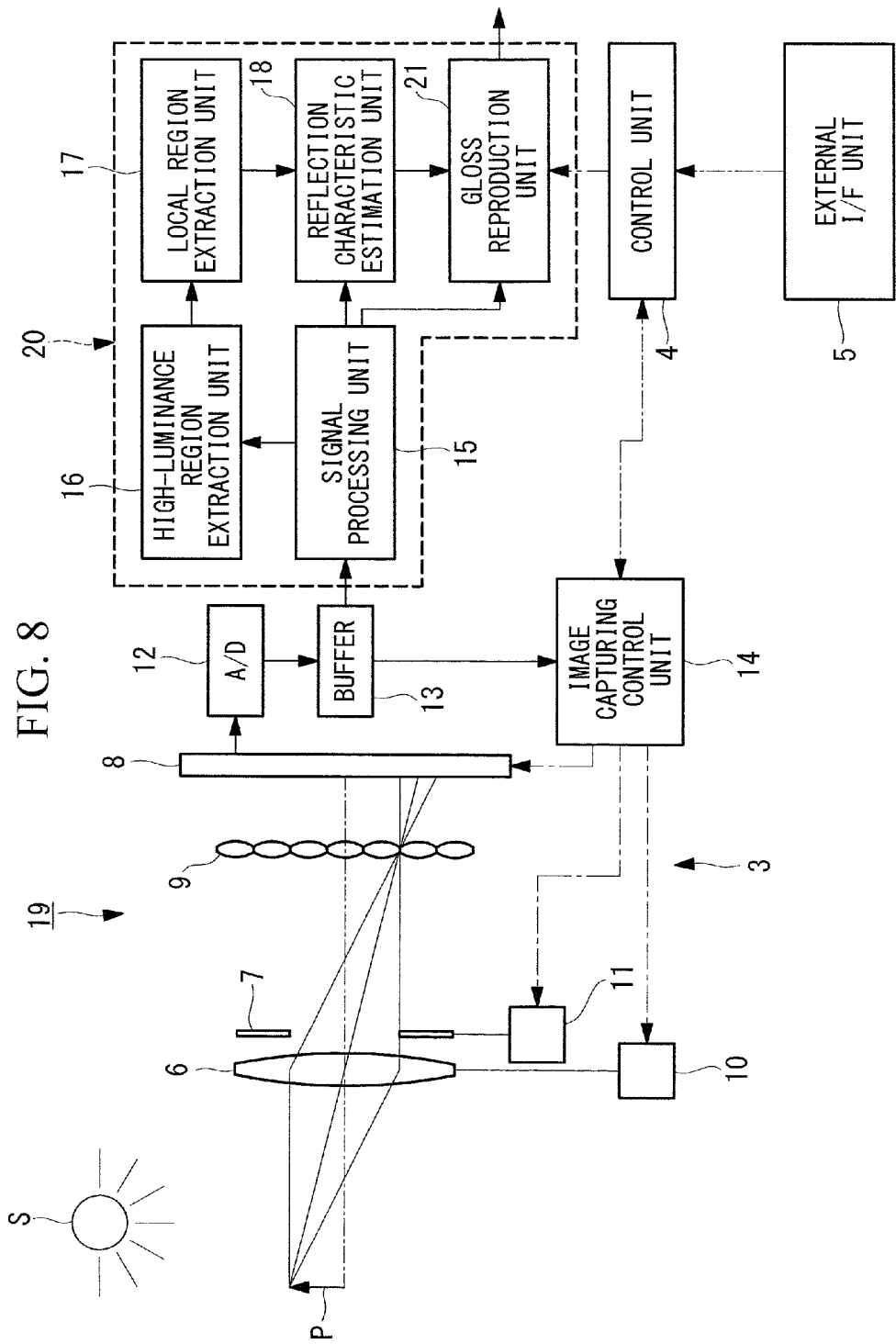
FIG. 8 is an overall view illustrating an imaging device according to a second embodiment of the present invention.
Figure 9:
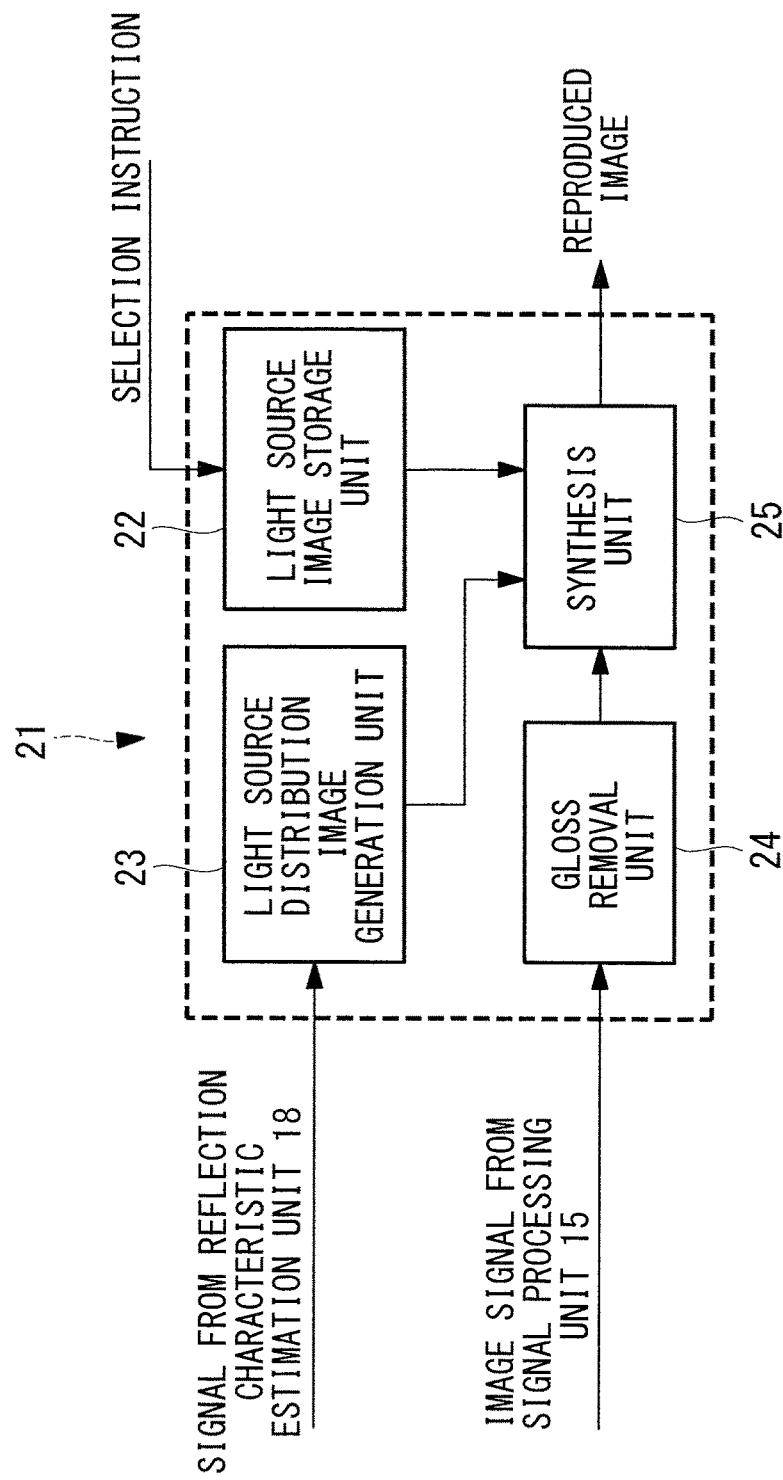
FIG. 9 is a block diagram illustrating a gloss reproduction unit in the imaging device illustrated in FIG. 8.

The imaging device 19 according to the present embodiment differs from the imaging device 1 according to the first embodiment in that the image processing apparatus 20 includes a gloss reproduction unit (reproduced image generation unit) 21, as illustrated in FIGS. 8 and 9.

The gloss reproduction unit 21 generates, when an image signal sent from a signal processing unit 15 has been observed under a light source different from that during shooting, an image signal using a reflection characteristic of a subject P estimated by a reflection characteristic estimation unit 18, as illustrated in FIG. 9.

More specifically, the gloss reproduction unit 21 stores respective images of one or more light sources (virtual light sources) S previously prepared in a light source image storage unit 22, and includes a light source distribution image generation unit 23 which generates a light source distribution on the subject P using the image of the light source S selected from an external I/F unit 5 and the reflection characteristic of the subject P estimated by the reflection characteristic estimation unit 18, as illustrated in FIG. 9.

The light source distribution image generation unit 23 generates the light source distribution by multiplying the estimated reflection characteristic and the selected light source image, as illustrated in FIG. 10.

Figure 11:
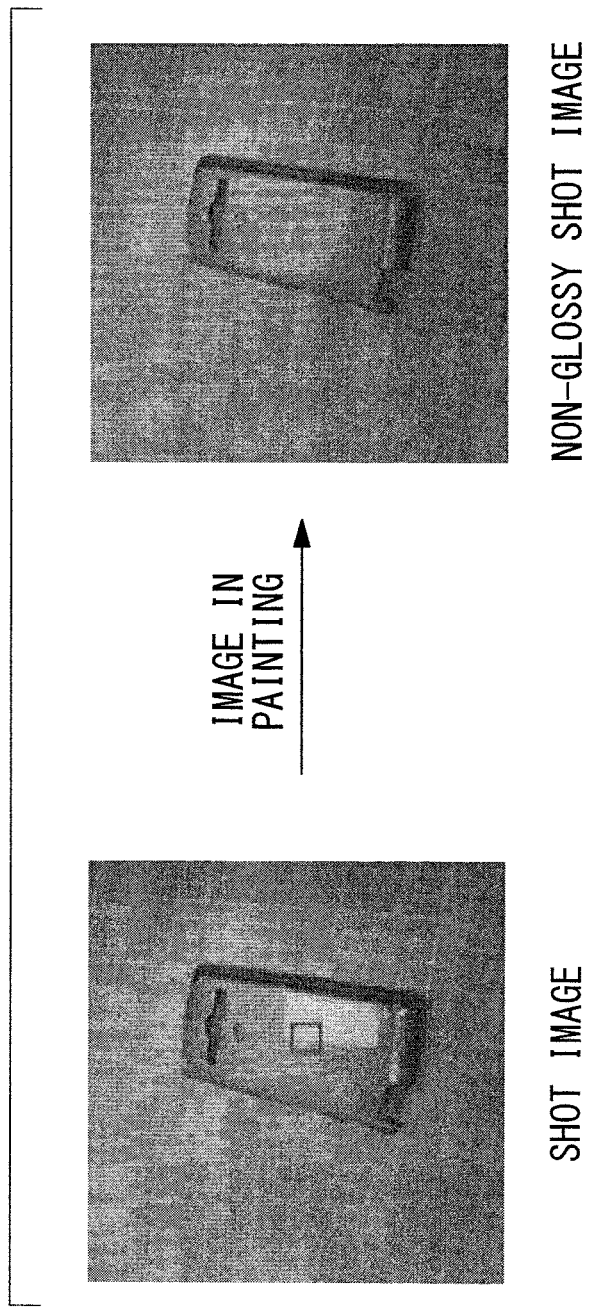
FIG. 11 is a diagram illustrating a model of a non-glossy shot image generated by a gloss removal unit in the imaging device illustrated in FIG. 8.

The gloss reproduction unit 21 includes a gloss removal unit 24 which generates a shot image from which a glossy portion is removed by a known image painting method or the like for the image signal sent from the signal processing unit 15, as illustrated in FIG. 9. The gloss removal unit 24 removes the glossy portion included in the image signal, to generate a non-glossy shot image, as illustrated in FIG. 11.

Figure 12:
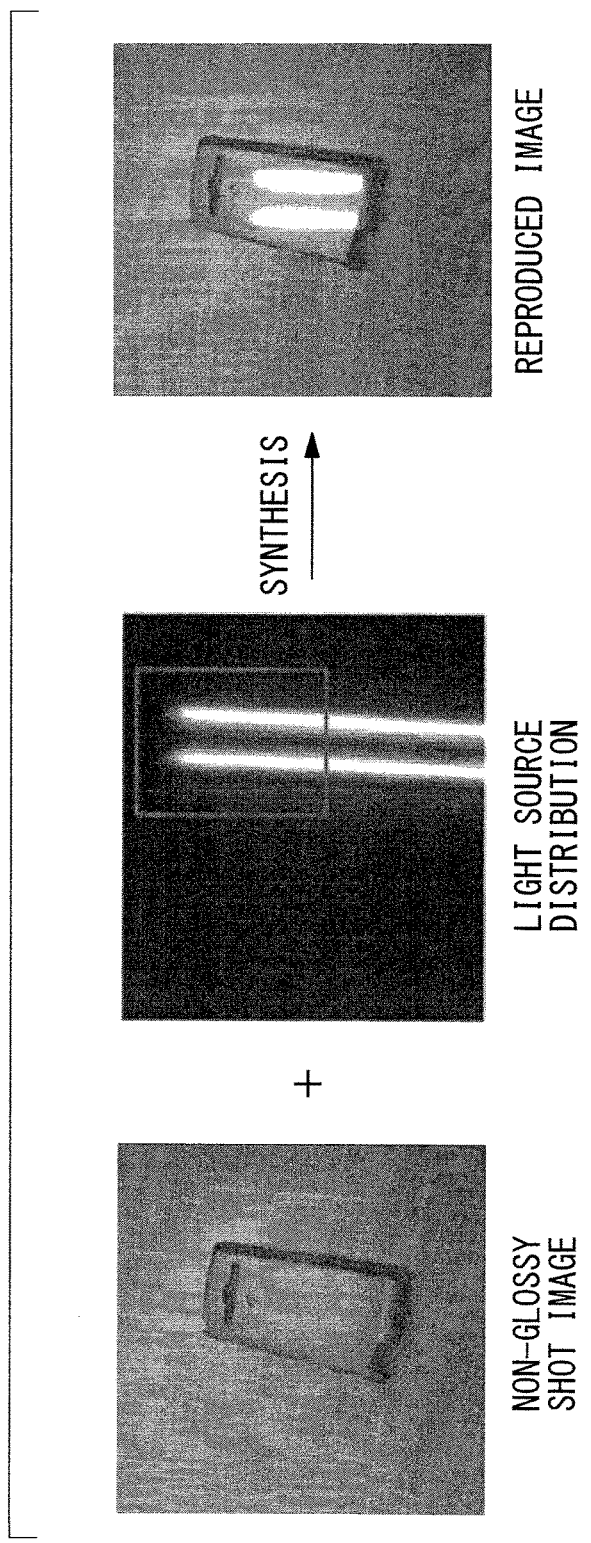
FIG. 12 is a diagram illustrating an example of a reproduced image generated by a synthesis unit in the imaging device illustrated in FIG. 8.

The gloss reproduction unit 21 includes a synthesis unit 25 which synthesizes the light source distribution generated in the light source distribution image generation unit 23 with the shot image generated in the gloss removal unit 24, to generate a reproduced image, as illustrated in FIGS. 9 and 12.

An image processing method using the image processing apparatus 20 according to the present embodiment includes generating a light source distribution by multiplying a reflection characteristic estimated in the reflection characteristic estimation unit 18 and a light source image selected from among light source images stored in the light source image storage unit 22 (a light source image generation step), generating a non-glossy shot image in the gloss removal unit 24 (a gloss removal step), and synthesizing the generated shot image and light source distribution (a synthesis step). Thus, the imaging device 19, the image processing apparatus 20, and the image processing method according to the present embodiment have an advantage in that a reproduced image as observed under a different virtual light source from that during shooting can be acquired simply and with high accuracy.

In the foregoing, the light source distribution is generated from the stored image of the light source S and reflection characteristic. Thus, a reproduced image focused on the subject P is generated. However, reproduced images, which differ in focal position, may be generated by generating a light source distribution on which a PSF obtained when the subject P is not focused on is further accumulated, as illustrated in FIG. 3B. That is, when a distance from a focal position of each of the portions of the subject P is considered, a PSF of an optical system can be calculated. A reproduced image obtained when the subject P is not focused on can be generated using the calculated PSF other than a delta function.

The inventors have arrived at the following aspects of the invention.

According to an aspect of the present invention, there is provided an image processing apparatus, including a high-luminance region extraction unit which extracts high-luminance regions serving as regions each having a higher luminance than a predetermined threshold value in a plurality of image signals obtained by irradiating a subject with light emitted from a known light source and by shooting reflected light from the subject at a plurality of viewpoints different from one another, a local region extraction unit which extracts local regions each of which is in the most in-focus state in its portion of the subject using the plurality of high-luminance regions extracted in the high-luminance region extraction unit, and a reflection characteristic estimation unit which estimates a reflection characteristic of the subject using respective light source characteristics of the high-luminance regions in the local regions extracted in the local region extraction unit.

According to the aspect, in the plurality of image signals obtained by irradiating the subject with the light emitted from the known light source and respectively shooting images of the reflected light from the portions of the subject at the plurality of viewpoints different from one another, the high-luminance regions are compared with the threshold value in the high-luminance region extraction unit, and the high-luminance regions each having a higher luminance than the threshold value are extracted. The extracted high-luminance regions are compared among the image signals in the local region extraction unit, and the local regions which are in the most in-focus state in the portions of the subject are extracted.

That is, the plurality of image signals obtained by the shooting from the plurality of viewpoints different from one another include image signals of the reflected light from the portions of the subject respectively arranged at positions which differ in depth. When the image signals of the reflected light are compared with one another to extract the local regions which are in the most in-focus state, the local region which is in a in-focus state in each of the portions, which differ in depth, can be extracted within any one of the image signals. Therefore, in the local regions, the reflection characteristic estimation unit can consider a point spread function of a defocused optical system as a delta function by using the respective light source characteristics of the high-luminance regions, and can estimate the respective reflection characteristics of the portions of the subject with high accuracy.

In the above-described aspect, the reflection characteristic estimation unit may use an edge gradient of the light source as the light source characteristic of the high-luminance region.

Thus, the reflection characteristic of each of the portions of the subject can be simply estimated with high accuracy by using the edge gradient of the light source as the light source characteristic easily represented.

In the above-described aspect, the reflection characteristic estimation unit may estimate a point spread function of specular reflection as the reflection characteristic.

Thus, the reflection characteristic estimation unit can calculate the point spread function of specular reflection serving as the reflection characteristic using the acquired image signal, the point spread function of the optical system, and the light source characteristic. When the image signal in the local region focused on is used, the point spread function of the optical system can be considered as a delta function, and the reflection characteristic can be simply calculated.

In the above-described aspect, the image processing apparatus may include a reproduced image generation unit which generates a reproduced image of the subject under a virtual light source based on the reflection characteristic estimated by the reflection characteristic estimation unit and an image of the virtual light source.

Thus, the reproduced image generation unit can generate the reproduced image obtained when the subject has been observed using the virtual light source different from the light source used to estimate the reflection characteristic without performing shooting using the virtual light source.

In the above-described aspect, the reproduced image generation unit may generate the reproduced image based on a distance from a focal point at each of points of the subject.

Thus, the point spread function of the optical system can be calculated based on the distance from the focal point at each of the points of the subject, and the reproduced images, which differ in focal position, can be generated.

According to another aspect of the present invention, there is provided an imaging device, including an image signal acquisition unit which acquires a plurality of image signals obtained by irradiating a subject with light emitted from a known light source and by shooting reflected light from the subject at a plurality of viewpoints different from one another, and any one of the above-described image processing apparatuses which estimate a reflection characteristic of the subject from the plurality of image signals acquired by the image signal acquisition unit.

According to the aspect, the reflected light emitted from the known light source and reflected on each of portions of the subject is acquired as the plurality of image signals obtained by the shooting at the plurality of viewpoints different from one another by the image signal acquisition unit, and the respective reflection characteristics of the portions of the subject are estimated in the image processing apparatus based on the plurality of image signals. Thus, in a shooting scene where a subject having a depth is shot, the reflection characteristics of the portions of the subject can also be estimated with high accuracy.

In the above-described aspect, the image signal acquisition unit may acquire the image signals which are based on images obtained by combining a plurality of optical systems which differ in principal ray.

Thus, as the plurality of image signals obtained by shooting the reflected light on the subject from the plurality of viewpoints different from one another, the plurality of image signals obtained by the shooting from the plurality of viewpoints different from one another can be respectively easily obtained from a plurality of images which differ in parallax.

In the above-described aspect, the imaging device may include an imaging optical system which collects light from the subject, in which the plurality of optical systems may divide an exit pupil of the imaging optical system.

Thus, when the plurality of optical systems divide the exit pupil, the plurality of images each having a parallax can be acquired by one shot, and the plurality of image signals obtained by the shooting from the plurality of viewpoints different from one another can be respectively easily obtained using the acquired images each having a parallax.

In the above-described aspect, the plurality of optical systems may respectively have optical axes different from one another.

Thus, when the reflected light from the subject is passed through the plurality of optical systems, an incidence pupil of the imaging optical system may be easily divided so that the plurality of images each having a parallax can be acquired by one shot.

In the above-described aspect, the image signal acquisition unit may acquire the plurality of image signals by capturing images a plurality of times while changing a focal length of the imaging optical system.

Thus, the plurality of image signals respectively focused at different focal positions can be easily obtained without via the images each having a parallax.

According to still another aspect of the present invention, there is provided an image processing method, including a high-luminance region extraction step of extracting high-luminance regions serving as regions each having a higher luminance than a predetermined threshold value in a plurality of image signals obtained by irradiating a subject with light emitted from a known light source and by shooting reflected light from the subject at a plurality of viewpoints different from one another, a local region extraction step of extracting local regions each of which is in the most in-focus state in its portion of the subject using the plurality of high-luminance regions extracted in the high-luminance region extraction step, and a reflection characteristic estimation step of estimating a reflection characteristic of the subject using respective light source characteristics of the high-luminance regions in the local regions extracted in the local region extraction step.

In the above-described aspect, the image processing method may further include a reproduced image generation step of generating a reproduced image of the subject under a virtual light source based on the reflection characteristic estimated in the reflection characteristic estimation step and an image of the virtual light source.

The aforementioned aspects can achieve an advantageous effect of finding a reflection characteristic of each of the portions of a subject having a depth with high accuracy in shooting the subject.

REFERENCE SIGNS LIST 1, 19 Imaging device
2, 20 Image processing apparatus
3 Image acquisition unit (Image signal acquisition unit)
6 Imaging optical system
16 High-luminance region extraction unit
17 Local region extraction unit
18 Reflection characteristic estimation unit
21 Gloss reproduction unit (Reproduced image generation unit)
P Subject
S Light source (Known light source)

The invention claimed is:

1. An image processing apparatus comprising:
a high-luminance region extraction unit which extracts high-luminance regions serving as regions each having a higher luminance than a predetermined threshold value in a plurality of image signals obtained by irradiating a subject with light emitted from a known light source and by shooting reflected light from the subject at a plurality of viewpoints different from one another;
a local region extraction unit which extracts local regions each of which is in the most in-focus state in its portion of the subject using the plurality of high-luminance regions extracted in the high-luminance region extraction unit; and
a reflection characteristic estimation unit which estimates a reflection characteristic of the subject using respective light source characteristics of the high-luminance regions in the local regions extracted in the local region extraction unit.

2. The image processing apparatus according to claim 1, wherein the reflection characteristic estimation unit uses an edge gradient of the light source as the light source characteristic of the high-luminance region.

3. The image processing apparatus according to claim 1, wherein the reflection characteristic estimation unit estimates a point spread function of specular reflection as the reflection characteristic.

4. The image processing apparatus according to claim 1, further comprising a reproduced image generation unit which generates a reproduced image of the subject under a virtual light source based on the reflection characteristic estimated by the reflection characteristic estimation unit and an image of the virtual light source.

5. The image processing apparatus according to claim 4, wherein the reproduced image generation unit generates the reproduced image based on a distance from a focal point at each of points of the subject.

6. An imaging device comprising:
an image signal acquisition unit which acquires a plurality of image signals obtained by irradiating a subject with light emitted from a known light source and by shooting reflected light from the subject at a plurality of viewpoints different from one another; and
the image processing apparatus according to claim 1 which estimates a reflection characteristic of the subject from the plurality of image signals acquired by the image signal acquisition unit.

7. The imaging device according to claim 6, wherein the image signal acquisition unit acquires the image signals which are based on images obtained by combining a plurality of optical systems which differ in principal ray.

8. The imaging device according to claim 7, further comprising an imaging optical system which collects light from the subject,
wherein the plurality of optical systems divide an exit pupil of the imaging optical system.

9. The imaging device according to claim 7, wherein the plurality of optical systems respectively have optical axes different from one another.

10. The imaging device according to claim 8, wherein the image signal acquisition unit acquires the plurality of image signals by capturing images a plurality of times while changing a focal length of the imaging optical system.

11. An image processing method comprising:
a high-luminance region extraction step of extracting high-luminance regions serving as regions each having a higher luminance than a predetermined threshold value in a plurality of image signals obtained by irradiating a subject with light emitted from a known light source and by shooting reflected light from the subject at a plurality of viewpoints different from one another;
a local region extraction step of extracting local regions each of which is in the most in-focus state in its portion of the subject using the plurality of high-luminance regions extracted in the high-luminance region extraction step; and
a reflection characteristic estimation step of estimating a reflection characteristic of the subject using respective light source characteristics of the high-luminance regions in the local regions extracted in the local region extraction step.

12. The image processing method according to claim 11, further comprising a reproduced image generation step of generating a reproduced image of the subject under a virtual light source based on the reflection characteristic estimated in the reflection characteristic estimation step and an image of the virtual light source.

* * * * *